(12) United States Patent
Zakharov et al.

(10) Patent No.: US 9,526,431 B2
(45) Date of Patent: Dec. 27, 2016

(54) SYSTEM FOR NONINVASIVE OPTICAL MEASUREMENTS OF PHYSIOLOGICAL PROPERTIES IN TISSUE

(75) Inventors: Pavel Zakharov, Volketswi (CH); Mark Talary, Zurich (CH); Andreas Caduff, Schmerikon (CH)

(73) Assignee: BIOVOTION AG, Zurich (CH)

( * ) Notice: Subject to any disclaimer, the term of this patent is extended or adjusted under 35 U.S.C. 154(b) by 62 days.

(21) Appl. No.: 14/351,956

(22) PCT Filed: Oct. 19, 2011

(86) PCT No.: PCT/CH2011/000247
§ 371 (c)(1),
(2), (4) Date: May 19, 2014

(87) PCT Pub. No.: WO2013/056379
PCT Pub. Date: Apr. 25, 2013

(65) Prior Publication Data
US 2015/0190063 A1    Jul. 9, 2015

(51) Int. Cl.
*A61B 5/0295* (2006.01)
*A61B 5/024* (2006.01)
*A61B 5/1455* (2006.01)
*A61B 5/11* (2006.01)
*A61B 5/00* (2006.01)

(52) U.S. Cl.
CPC ......... *A61B 5/0295* (2013.01); *A61B 5/02416* (2013.01); *A61B 5/1107* (2013.01); *A61B 5/14551* (2013.01); *A61B 5/721* (2013.01)

(58) Field of Classification Search
CPC . A61B 5/0295; A61B 5/02416; A61B 5/1107; A61B 5/14551; A61B 5/721
See application file for complete search history.

(56) References Cited

U.S. PATENT DOCUMENTS

| | | | |
|---|---|---|---|
| 5,490,505 A | | 2/1996 | Diab et al. |
| 6,018,673 A | * | 1/2000 | Chin .................. A61B 5/14552 356/41 |
| 2005/0177046 A1 | | 8/2005 | Mills |
| 2009/0209834 A1 | | 8/2009 | Fine |
| 2011/0046462 A1 | * | 2/2011 | Ono ..................... A61B 5/0816 600/323 |

(Continued)

*Primary Examiner* — Catherine Voorhees
(74) *Attorney, Agent, or Firm* — Ladas & Parry LLP

(57) ABSTRACT

Embodiments of the present invention comprise systems and methods for noninvasion measurements of physiological properties of tissues. The system comprises a light emitter, an optical detector, a mechanical sensor and a processor. The light emitter is capable of emitting light of at least two different wavelengths and comprises at least one light source. The processor is capable of evaluating physiological properties of the tissues from measurements of the optical and the mechanical sensor. More precisely, the processor is capable of evaluating physiological properties of venous blood by using data measured by the mechanical sensor and the optical detector. For example, the oxygenation of venous blood can be measured. Furthermore, the systems can optionally comprise a light emitter which emits three wavelengths and/or the light emitter and the optical detector are arranged in reflection geometry and are located at a distance of at most 10 mm from each other.

1 Claim, 7 Drawing Sheets

(56) References Cited

U.S. PATENT DOCUMENTS

| | | | |
|---|---|---|---|
| 2011/0060200 A1* | 3/2011 | Bernreuter | A61B 5/14551 600/323 |
| 2011/0160549 A1 | 6/2011 | Saroka et al. | |
| 2011/0160554 A1* | 6/2011 | Megej | A61B 5/0507 600/365 |
| 2013/0053654 A1* | 2/2013 | Caduff | A61B 5/1455 600/301 |
| 2013/0131475 A1* | 5/2013 | Eisen | A61B 5/14552 600/324 |
| 2014/0016132 A1* | 1/2014 | Schmitz | A61B 5/14551 356/343 |

\* cited by examiner

SYSTEM FOR NONINVASIVE OPTICAL MEASUREMENTS OF PHYSIOLOGICAL PROPERTIES IN TISSUE

RELATED APPLICATION INFORMATION

This application is a 371 of International Application PCT/CH2011/000247 filed 19 Oct. 2011 entitled "System For Noninvasive Optical Measurements Of Physiological Properties in Tissue", which was published in the English Language on 25 Apr. 2013, with International Publication Number WO2013/056379, the content of which is incorporated herein by reference.

BACKGROUND OF THE INVENTION

The invention relates to a system for noninvasive optical measurements of physiological properties in tissue. In particular, the invention relates to systems and methods comprising a light emitter emitting light of at least two different wavelengths, an optical detector, and a processor. The processor is capable of evaluating physiological properties from measurements of the optical detector.

Systems as mentioned above are widely used to evaluate and monitor physiological properties in tissue such as oxygenation of blood and heart rate (HR) in a subject and especially in a human body. In the context of this document, tissue designates a biological tissue. A biological tissue is a collection of interconnected cells that perform a similar function within a subject. Furthermore, the tissue can comprise at least a part of a vascular system where the vascular system comprises vessels (so called blood vessels). Vessels are for example arteries, capillaries or veins. When a tissue comprises blood, then the blood is always comprised in vessels of the tissue.

All known systems have the disadvantage that they are only capable of evaluating the physiological properties with a satisfactory quality in tissue of human bodies while the human body is kept at clearly defined conditions during the evaluation. These conditions or restraints require the tissue and/or the human body to be kept at rest or to be held still for most systems. These conditions or restraints may even apply to a time period before the evaluation, for example the need for resting before taking a blood pressure and/or an oximetry reading. Some other systems actively stimulate the tissue in a defined way (for example mechanically through vibration and/or application of pressure on the tissue) or require the tissue and/or body to perform clearly defined movements. During the stimulation or defined movements, the tissue and/or body have to fulfill respective conditions.

The reason for such requirements (i.e. such conditions or restraints) is that movement of the tissue or the body during the evaluation causes motion artifacts in the measurements. The same applies to the orientation of the tissue (i.e. whether the surface of the tissue is for example horizontally or vertically oriented). Changes in the orientation of the tissue lead to artifacts. These movement and/or orientation artifacts can for example be caused by a change in blood flow in the tissue or a shift in tissue layers and can be induced directly or indirectly to the tissue. Only clearly defined motions and/or orientations lead to measurements or variations of measurements which can be interpreted using the systems in the state of the art.

Systems with sensors which are attached to a fingertip and which measure light which is transmitted through the fingertip are known and widely used. These systems suffer from movement and/or orientation artifacts and other disadvantages as described above or they try to solve these issues by filtration of the measured signal after the measurement with complicated algorithms which produces a delay in the response.

It also has become known to use a mechanical sensor, such as an accelerometer, to determine whether the system is subject to motion by the user. The mechanical sensor is a sensor which measures mechanical forces, pressure and/or acceleration. Only data measured while the system is at rest are used.

A simple and reliable evaluation or monitoring of physiological properties of tissue by noninvasive optical methods is therefore not possible under real life conditions on moving subjects, especially when the subject movements occur constantly in irregular patterns. Throughout this text, subject stands for an organism and/or a body comprising the tissue which is to be measured. Especially, the subject can be a human body.

BRIEF SUMMARY OF THE INVENTION

It is an object of the invention to create a system for noninvasive optical measurements of physiological properties in tissue of the type mentioned initially, which overcomes at least partially at least one of the disadvantages mentioned above.

According to an aspect of the invention, a system for noninvasive measurements of physiological properties of tissue is provided. The system comprises an optical sensor, a mechanical sensor and a processor. The optical sensor comprises a light emitter and an optical detector. The light emitter is capable of emitting light of at least two different wavelengths and comprises at least one light source. The processor is capable of evaluating (and for example programmed to evaluate) physiological properties of the tissues from measurements of the optical and the mechanical sensor. More precisely, the processor is capable of evaluating physiological properties of venous blood by combining measurements from the mechanical sensor and the optical sensor.

The light emitter comprises at least one light source, for example at least one semiconductor light source. Such a light source could comprise a light emitting diode (LED), a super luminescent diode (SLD) and/or a laser diode (LD). One single light source can emit light at least of one wavelength, for example within a clearly defined range of a wavelength. The light emitter is capable of emitting light at least two wavelengths which are for example distinct and within a clearly defined range of a wavelengths. Optionally, a first range of a wavelengths is around an isosbestic point of oxygenated and reduced hemoglobin, and a second range of a wavelengths is away from the aforementioned isosbestic point and for example at a wavelength where the absorbance of oxygenated and reduced hemoglobin differ strongly.

An isosbestic point is a wavelength at which two chemical species (in the example above: oxygenated and reduced hemoglobin) feature the same absorbance. By measuring once at the isosbestic point and once away from it, the relative absorbance difference allows to differentiate between the two chemical species. In particular, the first wavelength can be in the infrared range of 770-830 nm (and especially 790-810 nm) and the second wavelength can be in the visible red and for example in the range of 630-690 nm (and especially 650-670 nm). An alternative isosbestic point is in a wavelength range around 568 nm, an alternative wavelength range with significant difference in light absorption between oxygenated and reduced hemoglobin is in the infrared between 900 nm and 950 nm.

Alternatively, the wavelength ranges can be selected away from isosbestic points, where absorption efficiencies of oxygenated and reduced hemoglobin are different. For wavelength ranges away from isosbestic points, it is advantageous if the relative absorbance differences between the two chemical species feature opposite signs in these wavelength ranges. For example, one range could be the aforementioned visible red range of 630-690 nm where reduced hemoglobin has a higher absorption than oxygenated hemoglobin. The second range in this example could be the aforementioned infrared range of 900-950 nm where reduced hemoglobin has a lower absorption than oxygenated hemoglobin.

The optical detector is capable of measuring the light emitted from the light emitter. In one embodiment, the optical detector can measure using temporal multiplexing which means that the optical detector can measure light emitted from the light transmitter with a first wavelength at a separate time than light emitted from the light transmitter with a second wavelength. In another embodiment, the optical detector can be capable of measuring at least two wavelengths separately and simultaneously. The optical detector can optionally have different parts which are sensitive to different ranges of wavelengths. The optical detector can for example measure light which interacted with wavelength selective elements—such as filters or reflective surfaces—after that the light interacted with the tissue. It is further possible to use more than one optical detector, for example for measuring light in different geometric configurations and/or for better statistics.

In the state of the art, it has been known to measure blood oxygenation of arterial blood by light sensor arrangements that comprise a light emitter and an optical detector for two different wavelengths: the light detected at a wavelength for example around 660 nm is the wanted signal, whereas a signal at an isosbestic point is used to subtract the influence that stems from varying hemoglobin concentrations on the wanted signal, for example due to heart pulse waves.

The invention proposes to use the measured signals of the optical sensor and the mechanical sensor in a different way. The invention takes advantage of the fact that pressure inside a venous vascular system of a subject is significantly lower than the pressure in an arterial vascular system. A vascular system comprises the venous vascular system and the arterial vascular system and encapsulates every vessel which contains blood in the subject. Veins smooth out variations in blood flow since venous vascular compliance (i.e. vascular flexibility of veins) is higher than arterial compliance (i.e. vascular flexibility of arteries). Furthermore, the venous system contains the major amount of blood.

When a pressure balance of a part of the subject or of the whole subject is disturbed by active or passive motion of the subject, by orthostatic changes i.e. changes of the subject or subject part position relative to a direction of gravitation (for example lying down of the subject or moving a part of the subject from a vertical to a horizontal position) and/or by external pressure (for example by applying additional pressure to the tissue) the part of the vascular system which is mostly affected is the venous vascular system, due to a relatively low baseline pressure of the venous vascular system and due to compliance i.e. to a relatively high flexibility of the venous vascular system. This generally leads to a relocation of venous blood which can be observed with the optical sensor. The relocation of venous blood can be used for an estimation of venous blood parameters. Contrary to this, methods known from the prior art use relocation of arterial blood due to heart beats (mostly by identifying a heart pulse wave) for an estimation of arterial blood parameters.

Using the data from the mechanical sensor in addition to the optical data, quantitative statements about the venous blood can be made. The relocation of venous blood, in contrast to relocation of arterial blood, strongly depends on parameters such as the orientation of the tissue and/or parts of the subject (for example whether an arm is positioned horizontally or vertically), muscle tension and/or pressure close to the tissue or movement of the tissue and/or parts of the subject. In addition, the venous blood oxygenation is generally unknown. Due to this, it so far was impossible to make quantitative statements about venous blood physiological properties—the state of the art sensor arrangements concentrate on the arterial blood oxygenation and heart pulse waves only.

It is an insight of the inventors of the present patent application that using a mechanical sensor in addition to the optical sensor, also properties of the venous blood can be addressed. Especially, an accelerometer, as an example for a mechanical sensor, can determine the orientation of the whole subject, a part of the subject or of the tissue and therefore of the vascular system. This allows to reproducibly utilize the relocation of venous blood due to changes of the orientation of the venous vascular system relative to the direction of gravitation caused by the motion of the subject. Similarly, a pressure sensor can account for blood volume variations in the tissue respectively in the vascular system which are caused for example by muscle contraction and/or relaxation.

Furthermore, in embodiments of the invention, movement induced signals (including orientation change induced signals) are used to purposefully address venous physiological properties. This can be done because the venous vascular system is more strongly influenced by the movements (including orientation changes) than the arterial vascular system. But whereas relocation of venous blood is an undesired effect which has to be reduced or eliminated in the prior art methods, the invention takes advantage of the relocation of venous blood. The invention therefore uses an aspect to measure physiological properties of tissue which is regarded as a disadvantage in the methods of the prior art.

The mechanical sensor can for example be integrated in the same housing with the optical sensor. The mechanical sensor can for example also be placed on the subject separately. For example, in one embodiment the mechanical sensor and the optical sensor can be attached to an upper arm of the subject with a flexible band as a single unit. In another embodiment the mechanical sensor and the optical sensor can be placed separately on a torso of the subject. A combination of several (for example different) mechanical sensors is possible and can be advantageous. The mechanical sensor is placed in such a manner that the mechanical sensor measures movement, orientation and/or pressure which can be related to the tissue which is measured with the optical sensor.

The optical sensor can be arranged in a transmission or in a reflection geometry. In transmission geometry, the tissue lies in a direct path between the light emitter and the optical detector. In transmission geometry, the path of light portions detected by the detector is mainly straight from the emitter, in addition to portions that are scattered. In reflection geometry, the light emitter and the optical detector are arranged on a first side of the tissue. The light which is emitted from the light emitter enters the tissue from the first side and exits the tissue after the interaction again towards the first side and is then measured by the optical detector that is placed aside the light emitter. Reflection geometry can be advantageous in case of a wearable system, because for transmission arrangements, firstly the light path has to be relatively short, and secondly the measurement results critically depend on the length of the light path, and this implies that the measurement is easily distorted by small movements of the system that for example is mounted on a fingertip.

The processor evaluates the physiological properties of venous blood from measurements of the optical and the mechanical sensor. The mechanical sensor measures a movement of the whole subject, of a part of the subject and/or of the tissue, an orientation of the whole subject, of a part of the subject and/or of the tissue and/or a force or a pressure applied to the whole subject, to a part of the subject or to the tissue and therefore to the vascular system. The mechanical sensor can optionally comprise an accelerometer, a pressure sensor, a strain gauge and/or other sensors. The pressure sensor can for example measure a pressure or a force applied to the tissue and/or a pressure or a force of the tissue coming from the tissue. The pressure sensor is especially capable of measuring the pressure with which the pressure sensor is pressed against the tissue. The strain gauge can for example measure changes of the dimensions of the tissue which can be related for example to a contraction or a relaxation of at least one muscle.

The processor processes the results of the measurements of the mechanical sensor. In embodiments, it may identify active periods during which the tissue is subject to a movement and/or a change in position. The measurements of the mechanical sensor allow correcting for motion artifacts and/or orientation artifacts during these active periods. In the prior art, correction for motion artifacts and/or orientation artifacts is mostly done by filtering out measurements which might include these artifacts.

As a first processing step, the processor combines the measurements of the mechanical and the optical sensors and derives the corresponding physiological properties of the venous blood in the measured tissue. The processor derives in this first step at least the venous blood relocations, which is only one of many physiological properties which can be measured. As a second processing step, the contribution of the venous blood relocations estimated in the first step is removed from the measured optical signal. The remaining optical signal after the second processing step can be used in a third processing step for further analysis to derive physiological properties of the tissue. In the third processing step, the remaining optical signal can for example be used for an analysis of arterial blood relocations originating from factors which are not directly related to motion. A factor which is not directly related to motion is for example the heart pulse wave. The physiological properties which are derived in the first and/or third processing step can be for example heart rate, heart rate variability, arterial and/or venous blood oxygenation and arterial photoplethysmographic (PPG) pulse amplitude. Blood oxygenation is the ratio of oxygenated hemoglobin concentration to total hemoglobin concentration in the blood. Blood oxygenation can be estimated for specific types and/or volumes of blood, for example for arterial blood or venous blood or specific compartments of arterial or venous blood.

The movements and/or changes in position of the tissue or parts of the tissue are not restricted to conditions in which the tissue is to be held still or is subject to defined stimulation. Rather, the physiological properties of the venous blood in this tissue can therefore be measured during regular daily routine and in everyday life. Even measurements during the sleeping periods can be performed, as the movements of a sleeping person i.e. changes in the sleeping position which normally occur irregularly during the whole sleeping period are generally sufficient to allow measurements during the movement and/or position change. The measurements can of course also be performed while the tissue is at rest or stimulated in a defined manner.

The physiological properties of venous blood are of interest because the venous blood has already interacted with the tissue. Therefore, it is possible to conclude physiological properties of the perfused tissue from the physiological properties of the venous blood. In many cases, the information about the perfused tissue can be extrapolated to gain information about a part of or about the whole subject comprising this tissue i.e. the whole organism or body comprising this tissue. One of the physiological properties of venous blood which can be measured is for example the oxygenation of venous blood ($SvO_2$). The optionally measured oxygenation of venous blood depends on different factors such as oxygenation of the corresponding arterial blood ($SaO_2$), blood flow in the perfused tissue and oxygen consumption in the perfused tissue. Once the oxygenation of the venous blood is measured, the other factors can be deduced from it.

In a tissue with low and/or constant oxygen consumption under normal conditions (such as in human skin while the subject is at rest or moderately moving), venous oxygenation can be used as a substitute of the arterial oxygenation since the difference in oxygen content i.e. the effective drop in the oxygen content from arterial to venous blood is known. The arterial oxygenation therefore can be calculated through adding the known difference to the venous oxygenation. If only trends are of interest (increase, decrease or stability of oxygenation in blood), then the venous oxygenation can be used without further calculation and still represents the trends of arterial oxygenation.

The substitute use of $SvO_2$ as $SaO_2$ can be an advantage for wearable monitoring on actively moving subjects (sportsmen, emergency workers, soldiers on the field, etc.) when the heart pulse wave is difficult to resolve on top of a background of motion-induced venous blood relocations. Without the heart pulse wave, the methods in the prior art cannot derive $SaO_2$. The invention allows to derive $SvO_2$ and thus to calculate $SaO_2$ under normal conditions.

On the other hand, in tissue not under normal condition, for example when oxygen supply of the subject respectively the body is compromised (e.g. due to blood loss) the blood flow to the less vital tissues (such as skin, subcutaneous layers, muscle, gastrointestinal tract) is reduced and thus the resulting venous oxygen content in such organs is significantly reduced. Thus the $SvO_2$ in such organs measured with the proposed method can be a sensitive marker of such events. Significant changes of $SvO_2$ can therefore be used to identify a transition from a tissue or a whole body under normal to a tissue or a whole body not under normal condition.

As an option, relative concentrations of one or more derivatives of hemoglobin other than $SvO_2$ can be investigated in the venous blood. For example, carboxyhemoglobin, methemoglobin and/or fetal hemoglobin can be investigated. These derivatives have specific absorption spectra in the visible and/or infrared regions and thus can be detected optically. The advantage of using the venous blood for the estimation of the derivatives other than oxyHb is that the content of the derivatives other than oxyHb in venous blood is generally similar to the content of the derivatives in arterial blood, while the venous blood volume variations caused by motion are higher (i.e. venous blood relocations caused by motion are more pronounced) than the changes induced by the heart pulse wave in the arterial volume. Thus the venous blood can potentially provide a higher signal to noise ratio than the arterial blood for such measurements. For the measurements of hemoglobin derivatives other than oxygenated hemoglobin, additional probing wavelengths can be introduced in order to allow for discrimination of different hemoglobin derivatives due to their specific absorption spectra.

Physiological properties of venous blood can be combined with physiological properties of arterial blood to derive additional parameters. Different methods to measure the physiological properties of arterial blood are known and described in the state of the art. It is possible to measure the physiological properties of arterial blood using the system described above (or only parts of it, for example by using the sensors, the data and/or the processor). In addition or as an alternative, is also possible to measure the physiological properties of arterial blood separately and independently.

For example, when $SaO_2$, $SvO_2$ and the blood flow are known, tissue oxygen consumption can be estimated according to Fick's principle as a product of the blood flow and oxygenation difference between $SaO_2$ and $SvO_2$. The blood flow can for example be derived from a PPG amplitude estimated with a system according to the invention or with alternative methods using the system according to the invention and/or other systems. Alternative methods using other systems are for example Laser Doppler Flowmetry (LDF) or measurements using a heat dissipation sensor.

Therefore, the measurement of physiological properties of venous blood additionally allows a better insight and more precise measurements of physiological properties of the tissue. But also the oxygenation of the arterial blood can be calculated with the use of the oxygenation of the venous blood in a more accurate and precise way since the measurement can account for changes in movement, position, pressure and/or perfusion. In general, the invention allows measurements of physiological properties of tissue using a non-invasive method suitable for real time application.

As an option, the processor is capable of evaluating a physiological property of venous blood using movement of blood in the tissue caused by natural movement of the tissue.

The physiological properties of venous and arterial blood and especially the oxygenation of venous and arterial blood can optionally be separated by the processor by using natural movement of the tissue which causes the blood in the tissue to move. The processor evaluates the measurements of the mechanical sensor and identifies movement of the tissue. The tissue movement can be induced by natural movements which occur in everyday life. This is called the indirect method.

The indirect method uses natural movement of blood i.e. relocation of the blood in the tissue due to natural movement of the tissue.

In addition or as an alternative, the tissue movement can also be induced by defined motions and/or through external stimulation. This is called the direct method. The direct method forces blood movement in the tissue, for example through arterial or venous occlusions or defined physical exercise for patients. A typical example for an external stimulation is a tilt table test (also called upright tilt testing), where the subject is attached to a table. Measurements of the subject are then performed while the table with the attached subject changes position from vertically oriented to horizontally oriented and vice versa.

One advantage of the indirect method is the possibility to measure the physiological properties of venous and arterial blood in real life conditions and without any restraints or conditions. This is more convenient than the direct method since the subject does not have to follow restrictions. Furthermore, the measurements can be performed in the usual environment of the subject. A patient i.e. a human being for example can be monitored during work, leisure time and/or while sleeping and is able to follow his usual and normal daily routine.

To identify movement of the tissue and/or within the tissue (for example movement of different tissue layers relative to each other), the processor evaluates the measurements of the mechanical sensor. The processor optionally can set an upper and/or lower threshold of movement of the tissue to define a range of movement of the tissue in which the processor evaluates the measurements of the optical and/or mechanical sensor. The processor is capable of evaluating the data of the optical and/or mechanical sensor in respect to the identified movement of the tissue.

As a further option, the system according to the invention is capable of detecting variations of lighting conditions and subtracting these variations from the measured optical signals. This is for example of special importance for wearable systems where the subject and the system can be exposed to different lighting conditions as during real-life activities of a human subject, especially when for example ambient lighting conditions vary strongly.

The lighting condition variations can for example be measured with a detector which is also used for a measurement of tissue attenuation. In such a case, the light emitter of the system should be disabled or an intensity of the emitted light should be modified in a predefined way during measurements of the lighting condition. Alternatively, lighting conditions can be monitored with at least one dedicated sensor which is for example not sensitive to the light from the emitter. The dedicated sensor for measurements of lighting conditions can optionally also be used for other measurements. In the case of a dedicated sensor which is not sensitive to the light from the emitter, the measurements of the lighting conditions can be performed simultaneously to the measurements of the system, which is of an advantage in the case of rapidly changing lighting conditions.

As a further option, the processor is capable of recognizing variations of the optical signal related to a heart pulse wave respectively to a heart beat and is capable of including these variations in the evaluation of physiological properties of the venous and/or arterial blood.

The processor is optionally capable of evaluating the measurements of the optical sensor and/or the mechanical sensor to estimate a heart rate and/or a heart pulse wave parameter such as phase, amplitude, transit time and other characteristics of a heart pulse wave. This can be performed for example with a photoplethysmographic approach, which is known in the state of the art. In the photoplethysmographic approach, changes in light attenuation which are associated with cyclical variations in concentration and orientation of red blood cells in a sampled microvascular volume are measured. The processor is capable of extracting a frequency and a phase of a heart cycle as well as other parameters of these cyclical variations with known algorithms.

The estimated heart rate and/or heart pulse wave parameter is then used to interpret the measurements of the optical sensor further. The heart rate and/or heart pulse wave parameter can show specific signal changes in the measured signals. With an estimated heart rate and/or heart pulse wave parameter these specific signal changes can be identified. If needed, the specific signal changes can be eliminated.

The measurements of the optical and/or mechanical sensor can also be interpreted specifically during at least a part of the time intervals while the specific signal changes of the heart rate and/or a heart pulse wave parameter occur. The measurements of the optical and/or mechanical sensor can for example be interpreted specifically only during a blood pressure increase which occurs during a heart beat respectively on the front of a heart pulse wave which is identified for example by a specific increase of the amplitude of the heart pulse wave. Through the estimation of the heart rate and/or a heart pulse wave parameter and the inclusion of this estimated heart rate and/or a heart pulse wave parameter in the evaluation of the physiological properties of venous and/or arterial blood through the processor, the measurements are more precise than without an estimation of such a heart rate and/or a heart pulse wave parameter.

In some cases and/or under certain conditions, the evaluation of the measurements is not possible at all without the estimation of the heart rate and/or a heart pulse wave parameter. In order to be able to evaluate a parameter of the heart pulse wave a sampling frequency of the optical signals should be at least 10 times higher than a frequency of the heart cycle. This results typically in the sampling frequency of at least 20 Hz.

As a further option, the light emitter is capable of emitting light of a third wavelength (in particular light in a green wavelength range) and the optical detector is capable of measuring the light of the third wavelength.

Generally, the third wavelength is preferably at an isosbestic point or alternatively at a point with a strong contrast between oxygenated and reduced hemoglobin signals.

In embodiments, where the first and second wavelength ranges are in the infrared and in the red part of the optical spectrum, respectively, the third wavelength may be in a green part of the spectrum.

Then, the range of the optionally emitted third wavelength is a green wavelength range (i.e. green range) which is in particular 500-600 nm and especially 540-570 nm. As an example, the third wavelength is 568 nm which is an isosbestic point for of oxygenated and reduced hemoglobin. Blood exhibits much higher absorption efficiency in the green range than in the red or the infrared ranges. Green light is thus very sensitive to variations of the amount of blood in the tissue. Measurements with green light are advantageously performed in reflection geometry. Optionally, the measurements with the third wavelength can be performed with a separate optical sensor (or separate optical detector) optimized for this particular wavelength. Such sensor (or detector) can potentially have a different geometry and different characteristic dimensions.

At an isosbestic point of oxygenated and reduced hemoglobin, both kinds of hemoglobin contribute the same signal intensity to the measured total signal. Therefore, measurements at such an isosbestic point represent measurements the total hemoglobin concentration and are not influenced by different and/or changing oxygenation of the hemoglobin. Thus such measurements at an isosbestic point represent indirectly measurements of the total blood perfusion. Measurements at isosbestic points may for example be used for measurements of a heart rate, and/or a heart pulse wave parameter. The heart rate and/or a heart pulse wave parameter can be used to ameliorate the measurements of the physiological properties of the tissue. For example, heart pulse wave effects and/or movement artifacts can be discriminated to ameliorate the measurements. Movement artifacts can be identified from characteristic changes in the heart rate and/or a heart pulse wave parameter.

In particular, measurements with light at an isosbestic point in the green range are suitable for measurements of the heart rate and/or a heart pulse wave parameter and/or other physiological properties of blood because of the high absorbance of blood for light in the green range and the resulting high sensitivity to this light. Especially, a signal measured in the green range may be indicative of the blood physiological properties of the uppermost tissue layers. The measured signal of the third wavelength is for example the total intensity of the third wavelength measured with the optical detector.

As a further option, the processor is capable of using a dynamic light scattering (DLS) technique to detect the heart rate and/or at least one heart pulse wave parameter.

Dynamic light scattering (DLS) techniques as for example laser Doppler or speckle correlometry allow the measurement of dynamics of material which scatters light, for example of a tissue matrix, fluids and/or particles in fluids and especially the dynamics of red blood cells in blood. DLS uses statistical analysis of intensity fluctuations of coherent light scattered from such material to derive parameters of dynamics of such material. By investigating statistical properties of temporal fluctuation of scattered coherent light it is possible to detect for example the heart pulse wave as time intervals with increased dynamics of the red blood cells. Higher dynamics can lead to shorter correlation times, to a broader spectrum of fluctuations or to a reduced contrast of time-integrated speckles. DLS techniques can be applied at low cost and in a noninvasive manner. One embodiment using the DLS technique for an estimation of the heart rate features at least one additional laser diode. In another embodiment, LEDs are replaced with laser diodes The DLS techniques can be used to recognize variations of the movement of blood instead, in combination with and/or parallel to measurements with green light.

As a further option, the system comprises at least two optical detectors for spatially resolved measurements.

The tissue might be heterogeneous, and different parts of the tissue might exhibit different behaviour and/or physiological properties. At least two optical detectors allow optical measurements which are spatially resolved. Each optical detector is capable of receiving the light from at least one light emitter for at least a short period of time. In one example, one light emitter emits light which is received by the two optical detectors simultaneously and continuously during the measurement. The spatially resolved measurements measure one or more specific parts of the tissue. This allows more precise measurements and reduces possible problems which occur when the optical detectors measure arbitrary parts of the tissue and/or measure an average value of many different parts of the tissue. Optionally, the same specific part of the tissue is measured repetitively in a short and/or long time period.

Alternatively, detectors with spatially addressable elements can be utilized, e.g. a charge coupled device (CCD) or complementary metal-oxide-semiconductor (CMOS) based camera detectors. The spatially addressable elements are spatially separated and independently functioning (sub-) detectors within such a detector comprising the addressable elements. In other words, such a detector comprises a multitude of small (sub-)detectors which measure independently of each other and are spatially separated.

The spatially resolved measurement can alternatively or complementary also be performed in other configurations than with two optical detectors, for example with only one sensor and at least two light sources, where the at least two light sources emit light alternatively and where they are spatially separated. In this way, the light emitted by the at least two light sources interacts in different ways with the tissue and/or interacts with at least partially different parts of the tissue before it is measured by the one or more optical detectors.

As a further option, the light emitter and the optical detector are arranged in a reflection geometry and are located close to each other.

The arrangement of the light emitter and the optical detector in reflection geometry and close to each other allow a measurement of only the upper layers of the tissue, since the light which interacts only with the upper layers of the tissue contributes more intensity to the total intensity of the measured signal. With the reflection geometry, light which penetrates to deeper layers of the tissue suffers in general from more attenuation, absorption and/or scattering and is therefore less intense than light which penetrates only the upper layers of the tissue.

In the case of measurements of skin, the upper layers which are measured correspond mainly to dermal layers. Besides that the light emitter and the optical detector are located close to each other, additional other factors can allow a measurement of only the upper layers of the tissue. One additional factor is for example length of the measurements i.e. a temporal detection limit. Temporal detection limits can ensure that the detector measures only a spatially selected part of the tissue. When measurements are for example much shorter than the timescale of the disturbing parameters, then the disturbing parameters change total values of measured signal but not relative changes of the measured signal and the disturbing parameters are therefore suppressed for measurements of relative changes of the signal. On the other hand, very short measurements can lead to low precision of a measured signal due to lack of statistics or even can be impossible when the measurement length is at or below a limit of detection. The length of the measurement also depends of the intensity of the emitted light. The higher the intensity of the emitted light, the shorter a measurement can be for the same statistics.

That the light emitter and the optical detector are located close to each other means in the context of this document that the light emitter emits light in a distance of 0.1-10 mm, especially 0.5 mm-4 mm from the optical detector.

With the light emitter and the optical detector are located close to each other, the sampling volume of the tissue is furthermore localized i.e. the measured part of the tissue is limited in size and its position known. The advantage of measurements constrained to the upper layers of the tissue are a lower sensitivity to tissue movement of lower layers, relative movements between different layers and/or other factors as mechanical influences or motion artifacts. This is also advantageous to avoid or minimize motion artifacts.

In one embodiment, the light emitter and the optical detector are located close to each other and the optical detector comprises a multitude of (sub-)detectors which measure independently of each other and which are spatially separated. This is for example the case for a segmented photodiode or a camera. Each of the (sub-)detectors i.e. segments can be located with a different distance to the light emitter, which results in a graded separation. Through measurements with graded separation and an according choice and/or treatment of the measured signals, measurement of only the upper layers of the tissue can be ensured.

As another option, the system comprises a dielectric sensor which allows the system to discriminate different tissue components and volume fractions.

The dielectric sensor allows the system to discriminate different tissue components such as blood, blood cells and tissue fluids and allows for an estimation of their corresponding volume fractions. When such information is accessible, the processor can include it in the evaluation of the measurements of the mechanical and/or optical detector and the estimation of the physiological properties of the tissue become more precise than without such information. But even without being used in the evaluation of the measurements of the mechanical and/or optical detector, this information can be combined with the measurement results to provide additional parameters of interest and to allow further analysis of the state and the properties of the tissue. Different types of tissue liquids and/or volume fractions can alternatively also be estimated by for example an additional optical detector for the water content, for example in the infrared spectral range, instead of a dielectric sensor.

Optionally, effects of the movement of the tissue and/or the subject can be characterized with different imaging modalities which are able to continuously monitor tissue morphology. Such modalities include ultrasound techniques, optical coherence tomography and microscopy techniques. Changes in structure and/or dimension of the vascular system observed with such modalities can be related to the measurements of the optical sensor in a way similar to a way to relate the measurements of the mechanical sensor to the measurements of the optical sensor as described in the paragraphs above. The corresponding blood parameters can be extracted as described in the way to relate measurements of the mechanical sensor to the measurements of the optical sensor.

According to another aspect of the invention, a method for measurements of physiological properties of tissue is provided. This method is particularly applicable in a system as described in the paragraphs above and comprises the steps: emitting light with at least two wavelengths, optically measuring the emitted light after the emitted light interacted with the tissue, performing a mechanical measurement of the tissue during and/or closely synchronized with the step of measuring optically, evaluating physiological properties of the tissue from the optical and the mechanical measurements. The method is characterized in that in the step of evaluating, a physiological property of venous blood is evaluated.

This method can optionally comprise that the step of measuring optically comprises performing at least two optical measurements simultaneously for spatially resolved measurements. As another option, in the step of measuring optically the light is penetrating only upper layers of the tissue. The advantages and further options of this method and alternatives to some options are described in the paragraphs above. Features of the method claims may be combined with features of the device (i.e. system) claims and vice versa.

According to another aspect of the invention, a system for noninvasive measurements of physiological properties of tissue is provided. This system comprises an optical sensor and a processor which is capable of evaluating physiological properties from measurements of the optical sensor. The optical sensor comprises a light emitter, and an optical detector. The light emitter is capable of emitting light of at least three different wavelengths and comprises at least one light source. This system is characterized in that the processor is capable of evaluating separate physiological properties of venous and arterial blood. Compared to the system described in the paragraphs above, this system does not necessarily but only optionally feature a mechanical sensor. However, all other advantages and options (and alternatives to the options) for the system described in the paragraphs above are also valid for and applicable to this system.

According to another aspect of the invention, a system for noninvasive measurements of physiological properties of tissue is provided. This system comprises an optical sensor and a processor which is capable of evaluating physiological properties from measurements of the optical sensor. The optical sensor comprises a light emitter and an optical detector. The light emitter is capable of emitting light of at least two different wavelengths and comprises at least one light source. This system is characterized in that the light emitter and the optical detector are arranged in a reflection geometry and are located close to each other in order to measure blood movement only in upper layers of the tissue, and that the processor may be capable of evaluating separate physiological properties of venous and arterial blood. Compared to the system described in the paragraphs above the paragraphs describing the method, this system does not necessarily, but only optionally feature a mechanical sensor and/or a third light source. However, all other advantages and options (and alternatives to the options) for the system described in the paragraphs above are also valid for and applicable to this system.

The invention has a wide range of potential applications within for example a medical environment, life-style physiological monitoring, safety physiological monitoring and/or research applications. The invention could for example be applied in (but is not limited to) the field of medical applications, in the case of cardiac problems, apnea/hypopnea, in sleep labs, for general monitoring of elderly people, independent living, smart home concepts, for life-style/physiological monitoring, for sleep monitoring, self-tracking, amateur sport and fitness, professional athletes (especially for an optimization of training), for dangerous professions, drivers, air controllers and operators of machines (to detect for example drowsiness), for stress and/or arousal detection and for energy expenditure monitoring. Furthermore, the invention could be applied in research, in clinical studies for example for drug development, for sleep studies and cardiovascular disease research.

BRIEF DESCRIPTION OF THE DRAWINGS

The subject matter of the invention will be explained in more detail in the following text with reference to exemplary embodiments which are illustrated in the attached drawings, in which.

The reference symbols used in the drawings, and their meanings, are listed in summary form in the list of reference symbols. In principle, identical parts are provided with the same reference symbols in the figures.

DETAILED DESCRIPTION

Figure 1:
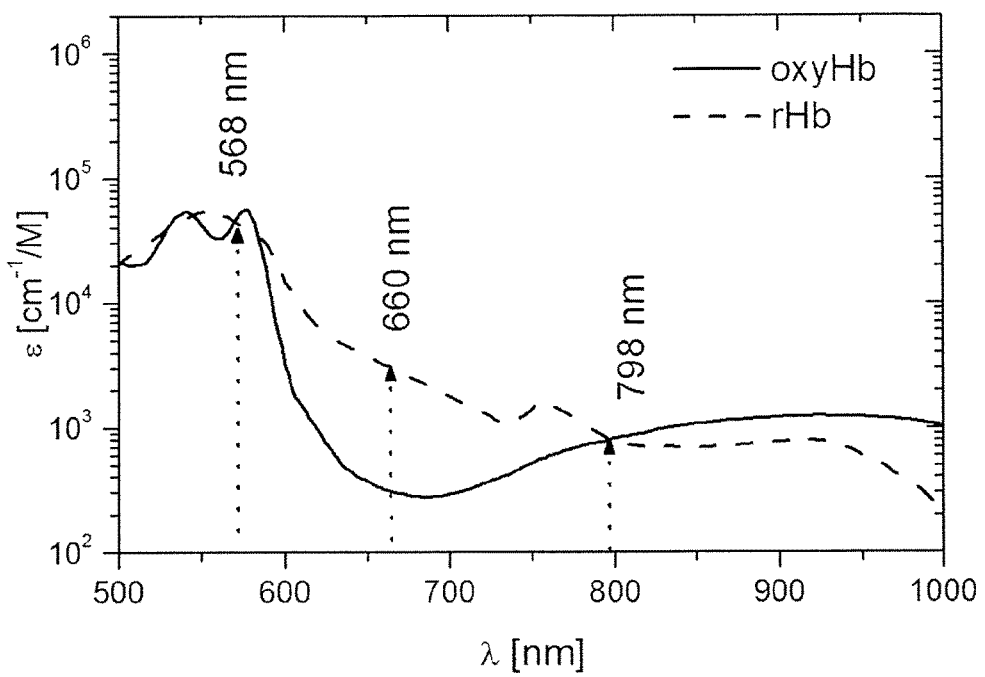
FIG. 1 shows a graph with the absorbance of oxygenated and reduced hemoglobin in dependence of the wavelength of light.

FIG. 1 schematically shows a graph with the absorbance of oxygenated hemoglobin (oxyHb) and reduced hemoglobin (rHb) in dependence of the wavelength of light. The vertical axis s of the graph represents the absorbance i.e. a molar extinction coefficient [$cm^{-1}$/M] which measures how strongly chemical species (in this case oxyHb and rHb) absorb light. The horizontal axis λ of the graph represents the wavelength [nm] of the light. Vertical dotted lines represent wavelengths chosen for one embodiment as described above. Two of these wavelengths are isosbestic points: a green isosbestic point at 568 nm and an infrared isosbestic point at 798 nm. Isosbestic points correspond to a wavelength where oxyHb and rHb exhibit the same absorbance. A red wavelength at 660 nm represents a point with a large difference i.e. a large contrast in the absorbance of oxyHb and rHb.

A difference in the absorbance of oxygenated and reduced hemoglobin as for example in the red range at 660 nm can be used for measurements of the relative amount of oxygen bound to hemoglobin. Typically at least two wavelengths with significantly different absorption efficiencies of rHb and oxyHb can provide this information. However, the presence of tissue components with unknown attenuation makes a quantitative interpretation of the measurements difficult.

In a scope of pulse oximetry as known in the state of the art, relative temporal variations of the measured signal intensity (and therefore an according attenuation in the tissue) caused by the heart pulse wave are measured with at least two wavelengths. The ratio of variations of the measured signal at all measured wavelengths can be then related to arterial blood oxygenation since a heart pulse wave is assumed to be present exclusively in the arterial vascular system. Contrary to this, the invention uses relative temporal variations of measured signal intensity due to relocations of venous blood (which are for example caused by motion of the tissue and/or the subject) for the estimation of the venous blood oxygenation. The venous blood oxygenation is estimated from relocations of venous blood (for example caused by movement of the tissue and/or the subject) while the arterial blood oxygenation is estimated from relocations of the arterial blood during the heart pulse wave which is caused by the heart beat.

FIG. 1 shows furthermore, that the absorbance of hemoglobin at the green isosbestic point is much higher than at the infrared isosbestic point. Thus the green light is more sensitivity to variations of a hemoglobin content. Generally, light at wavelength around the green isosbestic point have been found to provide a suitable reference signal in reflection measurements. Light at the green isosbestic point is therefore very well suited to be used for an evaluation of physiological properties of the tissue which are related to arterial blood, for example to estimate the heart rate, the heart rate variability and/or at least one heart pulse wave parameter which can be used for the enhancement of measurements on other wavelengths.

Figure 2:
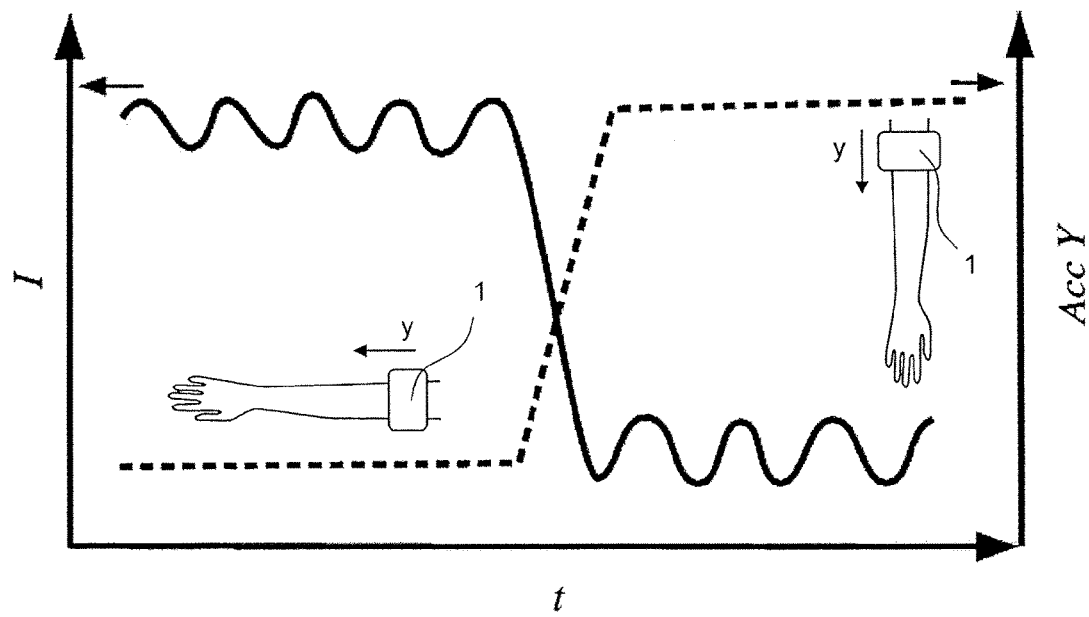
FIG. 2 schematically shows an effect of different orientations of the tissue on the intensity of measured light in reflection geometry.

FIG. 2 schematically illustrates an effect of different orientations of the measured tissue respectively the part of the subject comprising the tissue on the intensity of measured light in reflection geometry. A horizontal axis t in FIG. 2 represents time, a left vertical axis I represents intensity of light measured by an optical detector in a reflection geometry and a right vertical axis Acc Y represents acceleration in direction y measured by the mechanical sensor. These measurements are performed by a device 1 using a method and/or comprising an embodiment of a system according to the invention described above which include a mechanical sensor. The direction y is fixed relative to the device 1. Such a device 1 can be attached to an upper arm as shown in FIG. 2. Device 1 can be attached at other places, for example at the forearm, the wrists, the torso, the upper thighs and around the shins Device 1 features a mechanical sensor which is capable of measuring acceleration in direction y which in FIG. 2 is designated by an arrow.

On the left half of FIG. 2, the upper arm is positioned horizontally. In an idealised case the accelerator measures zero acceleration signal in direction of y, and the intensity I of light which is measured by the optical detector of device 1 is relatively high. The undulations of the measured intensity of light are caused by the heart pulse wave. When the upper arm is positioned vertically and downwards, as shown in the right half of FIG. 2, the amount of venous blood in the tissue probed by the sensor is increasing due to gravitation. The blood relocation is specific to the venous vascular system due to a significantly lower pressure of the venous vascular system compared with the arterial vascular system: the arterial blood flow with relatively high pressure in the arterial vascular system is not significantly changed by the relatively small effect of gravitation. But compared to the relatively low pressure of the venous vascular system, the effect of gravitations is relatively large, and the venous blood flow is significantly changed.

An increase of a venous blood volume when the upper arm is positioned vertically leads to an increase of absorbance of light (respectively to an increase of attenuation of light) which is interacting with the tissue and correspondingly to a decrease of the intensity I of the measured light. The accelerometer measures a gravitational acceleration in direction of y when the upper arm is positioned vertically. In short, the orientation of the tissue and/or the subject does influence the measured signal, and information related to the orientation of the tissue and/or the subject can be used to evaluate measurements which are performed with tissue at different and/or varying orientation.

FIG. 2 also illustrates that the measured signal comprises contributions of the arterial blood volume variations caused by the heart pulse wave and that the contribution of the venous blood relocations are caused by motion which means in this case a change of the orientation of the upper arm.

Device 1 as shown in FIG. 2 is an example of an embodiment of a system according to the invention described above. Device 1 is wearable, especially continuously wearable. Wearable means that device 1 is lightweight, unobtrusive, portable and can be worn without great discomfort. Preferably, device 1 is a standalone device and is not depending on other devices during the measurements. It is, however, not excluded that the device 1 is in permanent or non-permanent communication with other devices, attached to the subject, placed independently of the subject or carried by a subject.

Figure 3:
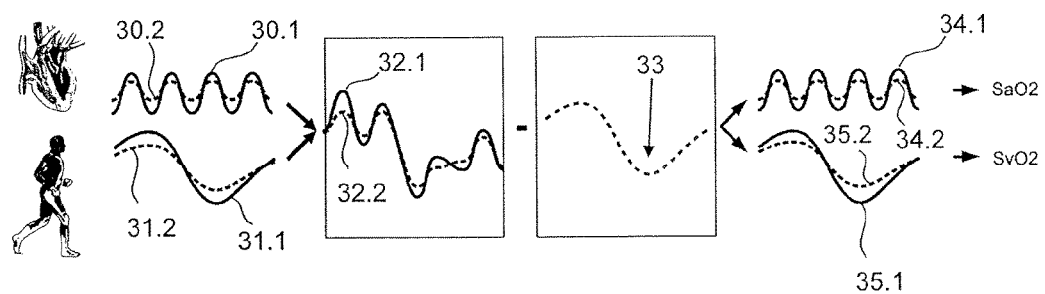
FIG. 3 schematically shows a superposition of arterial and venous blood volume changes and a way to separate them in optical measurements.

FIG. 3 schematically shows a superposition of arterial and venous blood volume changes and a way to separate them in optical measurements. From left to right, FIG. 3 shows separate initial arterial attenuation signals 30.1, 30.2 from arterial blood volume changes due to heart beat respectively the heart pulse waves and initial venous attenuation signals 31.1, 31.2 from venous blood volume changes due to activity, measured optical signals 32.1, 32.2, an accelerometer signal 33 and separated arterial portion signals 34.1, 34.2 and venous portion signals 35.1, 35.2. The initial arterial attenuation signals 30.1, 30.2 and the initial venous attenuation signals 31.1, 31.2 are a priori unknown. All signals except the accelerometer signal 33 in FIG. 3 are illustrated for two wavelengths: the signals with solid lines and the designation ending 0.1 represent a signal for a wavelength in the infrared range, and the signals with broken lines and the designation ending 0.2 represent a signal for a wavelength in the red range.

The measured optical signals 32.1 and 32.2 are a superimposed result of initial arterial attenuation signals 30.1, 30.2 and the initial venous attenuation signals 31.1, 31.2. In a simplest case in order to be able to separate signal portions from the arterial and from the venous blood, the accelerometer signal 33 is—after suitable calibration and/or sensitivity correction—subtracted from the measured signals 32.1, 32.2. The subtraction of the accelerometer signal 33 corrects for the influence of venous blood and results in arterial portion signals 34.1, 34.2 which represent arterial properties. A subtraction of the arterial portion signals 34.1, 34.2 from the measured signals 32.1, 32.2 then may provide venous portion signals 35.1, 35.2 representing properties of venous blood.

It is also possible to use more sophisticated approaches than a mere subtraction. Especially, the accelerometer signal may be statistically correlated with the measured optical signals. Signal portions of the optical signals that are correlated with the accelerometer tend to be of a venous origin, whereas uncorrelated signal portions are more of an arterial origin. Even more in general, other suitable algorithms that have the three signals as input and physiological properties as output are feasible. For example, it is possible to apply multivariate analysis (and multiple regression analysis in particular) to investigate the relation of intensity variations of red and infrared light which are correlated with the measurements of the mechanical sensor. Variations of the frequency of the heart rate not associated with mechanical movements can be attributed to the heart pulse wave and can be used for the estimation of physiological properties of arterial blood. Thus from the relation of the arterial portion signals 34.1, 34.2 and the venous portion signals 35.1, 35.2, physiological properties of the arterial respectively venous blood can be deduced.

Figure 4:
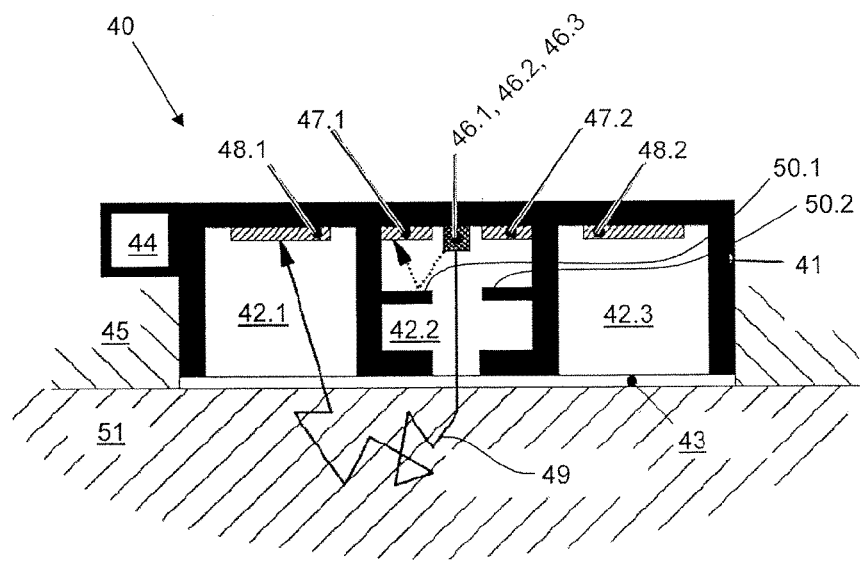
FIG. 4 schematically shows a cross section of an embodiment of the invention as a side view.

FIG. 4 schematically shows a cross section of one possible embodiment of the invention as a side view. The system 40 is comprised in the device 1. The system 40 comprises a frame 41 with three compartments 42.1-42.3: two light detector compartments 42.1, 42.3 and one light emitter compartment 42.2 between the light detector compartments 42.1, 42.3. The compartments 42.1-42.3 are formed on sides and top by the frame 40. At the bottom, the compartments 42.1-42.3 are closed by a glass plate 43. An acceleration sensor 44 is attached to the frame 41 such as all movements which affect the frame 41 and its content are measured by the acceleration sensor 44. Furthermore, the acceleration sensor 44 is capable of measuring the orientation of the frame 41. Frame 41 and acceleration sensor 44 are comprised in a substrate 45.

The light emitter compartment 42.2 is arranged between the two light detector compartments 42.1 and 42.3 and comprises the light emitter. The light emitter comprises three LEDs 46.1, 46.2, 46.3 which emit light at three different wavelengths and which are attached to the top of the light emitter compartment 42.2. A wavelength of light emitted by a first LED 46.1 is in the red range which is between isosbestic points and a wavelength of light emitted by a second LED 46.2 is in the infrared range at an isosbestic point. A third LED 46.3 emits light of the third wavelength close to an isosbestic point in the green range. Measured signals of the red and infrared (i.e. first and second) LEDs 46.1 and 46.2 are used for an estimation of the ratio of oxygenated haemoglobin, while a measured signal from the third, green LED 46.3 is used for the estimation of heart rate. The heart rate is used for the enhancement of the measured signals of the other wavelengths (red and infrared).

The light emitter compartment 42.2 also comprises two monitoring photodiodes 47.1, 47.2 which are either arranged in direct line of sight to the LEDs 46.1, 46.2 and 46.3 or as shown in FIG. 4 at the side of the LEDs 46.1, 46.2 and 46.3. The first and second monitoring photodiodes 47.1, 47.2 receive light emitted from the LEDs 46.1, 46.2, 46.3 through reflective elements 50.1, 50.2. Signals of both monitoring photodiodes 47.1, 47.2 are combined and they act as one single multicomponent detector. Alternatively, different monitoring photo diodes could measure different wavelengths in another embodiment of the invention. The combined measured signal of the monitoring diodes 47.1, 47.2 is used as reference signal accounting for intensity variations of the light emitted by the light emitter and more specifically by the LEDs 46.1, 46.2, 46.3. They may in addition or as an alternative be used for calibration purposes.

A first light sensor compartment 42.1 comprises a first signal photodiode 48.1 and a second light sensor compartment 42.3 comprises a second signal photodiode 48.2. The signal photodiodes 48.1, 48.2 are attached to the frame 41 in their compartments 42.1, 42.3. In analogy to the monitoring photodiodes 47.1, 47.2, the signals of photo diodes 48.1, 48.2 are combined and both act as a single multicomponent detector. Alternatively, different photo diodes could measure different wavelengths in another embodiment of the invention. Light emitted by the LEDs 46.1, 46.2, 46.3 is partly reflected by the reflective elements 50.1, 50.2 and partly passes a gap between the reflective elements 50.1, 50.2, as illustrated by an exemplary photon path 49. The light passes a second gap which is similar to the gap between the reflective elements 50.1, 50.2 and which is formed by the frame 41. Both gaps collimate the emitted light beam. After having passed the second gap, the light passes the glass 43 downwards and interacts with tissue 51, which is in direct contact with the glass 43.

After interaction of the emitted light with the tissue and diffuse propagation of the light in the tissue, some part of light passes (for example along a photon path 49) the glass 43 upwards and enters the light sensor compartments 42.1. In this light sensor compartment 42.1, the light is received and measured by the signal photodiode 48.1. Other photon paths will lead to the other sensor compartment 42.3, in analogy to the depicted photon path; the number of scattering/reflection events can be anything greater than or equal to one.

In this embodiment the measurements are to be performed with temporal multiplexing, i.e. the measurement is performed with one wavelength at a time. For example, firstly the repetitive sampling of green light can be performed when the third LED 46.3 is activated and an analog-digital converter (ADC) makes a repetitive simultaneous sampling of the intensity detected by the signal diodes 48.1, 48.2 and the monitoring photodiodes 47.1, 47.2. Such a sampling of light in the green range can be called a green block measurement. Furthermore, in order to allow for a correction for variations of ambient light, a periodical sampling of intensity with deactivated LEDs 46.1, 46.2, 46.3 can be performed. In a simplest case, the LEDs 46.1, 46.2, 46.3 can be set to emit light with a 50% duty cycle and the ADC measurements made while the LEDs 46.1, 46.2, 46.3 are not emitting light are used to correct the measured signal i.e. the light intensity detected while the LEDs 46.1, 46.2, 46.3 are emitting light to account for ambient light variations. The corrected signal can then be further used for the estimation of the heart rate and other physiological parameters.

Since signals measured in the red and infrared range are used in combination for the estimation of physiological parameters of the tissue and especially of physiological parameters of blood, their sampling should be performed in a sequential and interleaved fashion and form a measurement block. In a simplest case, the first and second LEDs 46.1, 46.2 (emitting light in the red and infrared range) are switched on and off consecutively and alternating while the ADC sampling of the corresponding signals is performed. This means that only either the first LED 46.1 or the second LED 46.2 is emitting light at any time and that the first LED 46.1 is switched off when the second LED 46.2 is switched on and vice versa. The measurements with the accelerometer sensor 44 are performed in parallel to the optical sampling i.e. to the sampling of the signal photodiodes 48.1, 48.2. Furthermore, the ambient light can be sampled periodically with all LEDs 46.1, 46.2, 46.3 switched off. The ambient light signal is furthermore used to correct the signals measured in the red and infrared range for varying ambient light conditions.

With the embodiment shown in FIG. 4, the sampling of a green block of measurements (i.e. sampling of measurements of light in the green range as described above) and a red/infrared block (i.e. sampling of measurements of light in the red and infrared range as described above) is performed sequentially.

Alternatively, the sampling of all three wavelengths as well as ambient light measurements can be performed in one single block, when the green, red, infrared and ambient light channels are sampled sequentially and repeatedly. In this case the measurement system should be able to sample with a sampling frequency which is at least four times higher than the minimum sampling frequency for a case of sampling of a single channel. The minimum sampling frequency for sampling of a single channel is typically 20 Hz.

If the system incorporates two or more individually operated optical sensors, sampling of the green channels and red/infrared channels can be performed in parallel. This increases the performance of the filtering method of signals in the red and infrared range with the heart rate obtained from the green measurements, since both measurements are performed at the same time.

Figure 5:
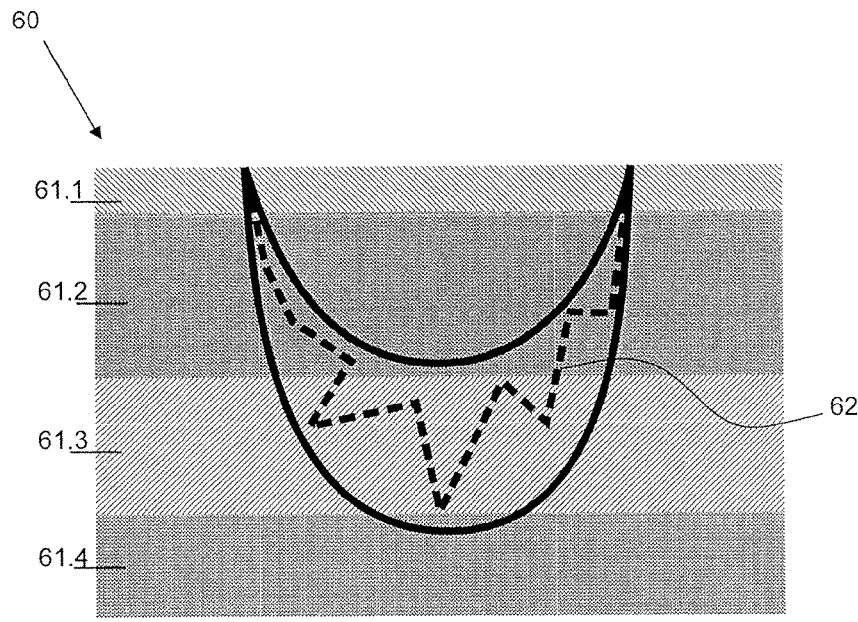
FIG. 5 shows a schematic representation of light propagation in skin.

FIG. 5 shows a schematic illustration of light propagation in human skin 60. The human skin 60 comprises different layers 61.1-61.4, and light can propagate through different layers 61.1-61.4. FIG. 5 shows an example of four layers 61.1-61.4, and these four layers 61.1-61.4 are the layers closest to the skin surface. The illustrated photon path 62 in reflection geometry interferes with three layers 61.1-61.3, more specifically with the three layers 61.1-61.3 closest to the skin surface. Solid lines designate the boundaries of statistically most probable paths which are likely to be taken by the photons emitted from S and detected at D.

Statistically, the proportion of photon paths that penetrate deeply in the tissue (i.e. the skin 60) compared to photon paths that do not penetrate deeply depends on a distance r between a light emitter S (i.e. a source) and an optical detector D in reflection geometry. The longer the distance r, the larger the portion of received photons that have penetrated deeply. Thus, the longer the distance r (in reflection geometry), the larger the portion of photons that have been scattered by different tissue layers. In the event of motion of the subject, the motion causes distortions, because the different layers will be displaced with respect to each other. With a smaller source-detector distance r the propagation will be limited to the upper layers of the skin (as shown for example by the photon path 62 in the upper three skin layers 61.1-61.3), and thus the sensitivity to motion artefacts caused by the skin motion will be decreased The measurements of FIGS. 6-9 were performed with a system 40 as described in FIG. 4 attached to the upper arm as illustrated in FIG. 2.

Figure 6:
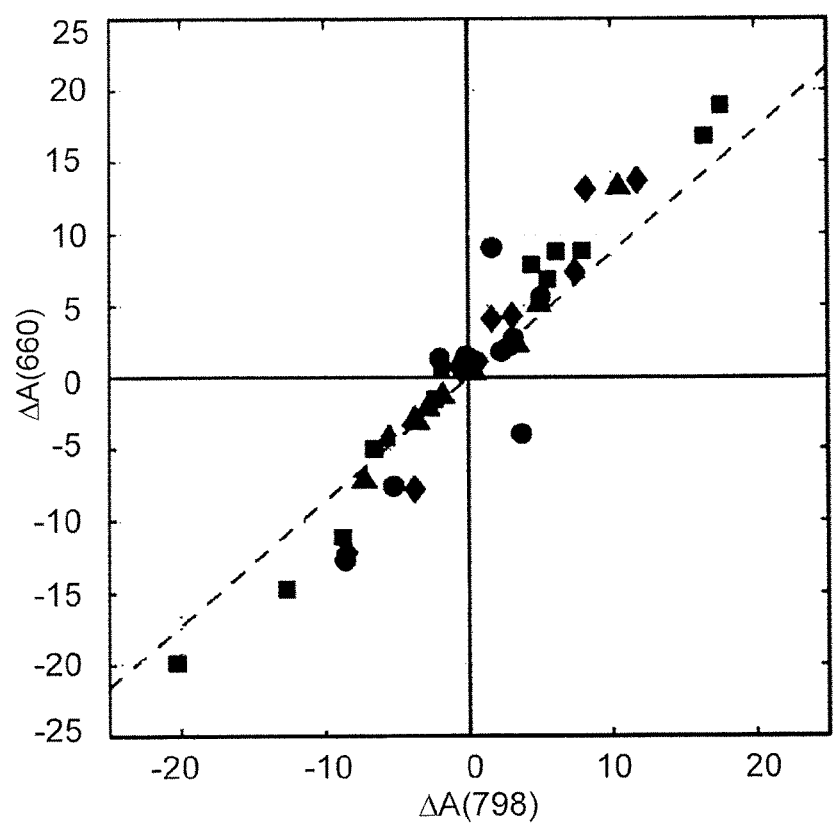
FIG. 6 shows a graph of an attenuation of infrared light plotted against an attenuation of red light during different exercises.

FIG. 6 shows in a graph an attenuation of red light during different exercises plotted against an attenuation of infrared light measured simultaneously. In FIG. 6, the horizontal axis $\Delta A$ (798) designates changes in attenuation of infrared light, and the vertical axis $\Delta A$ (660) designates changes in attenuation of red light. Both attenuations are measured with a device according to the invention which means that the attenuations are deduced from the calculated venous blood signal (shown as venous portion signals 35.1, 35.2 in FIG. 3). There is a clearly visible relation of changes in the attenuations of infrared and red light during exercises, visualised through a broken line. Each symbol shape represents measurements of a different subject i.e. of a different human volunteer. From a slope of the broken line, an averaged oxygenation ratio of 0.87 can be deduced for the venous blood in the tissue of all volunteers. The oxygenation is calculated by linear regression with a coefficient of determination $R^2$ of 0.9 which indicates that the fit by linear regression is a good approximation of the measurements and further indicates that a difference in the oxygenation between different subjects and different experiments is relatively small. The averaged venous oxygenation ratio of 0.87 obtained is lower than the arterial blood oxygenation ratio which is generally above 0.95, also during exercises. This demonstrates the principle of operation of the invention and supports the assumption that the attenuations shown in FIG. 6 are deduced from a venous blood signal. In consequence, this also supports the assumption that the variations of the volume of the blood caused by exercise are mainly due to relocation of the venous blood.

Figure 7:
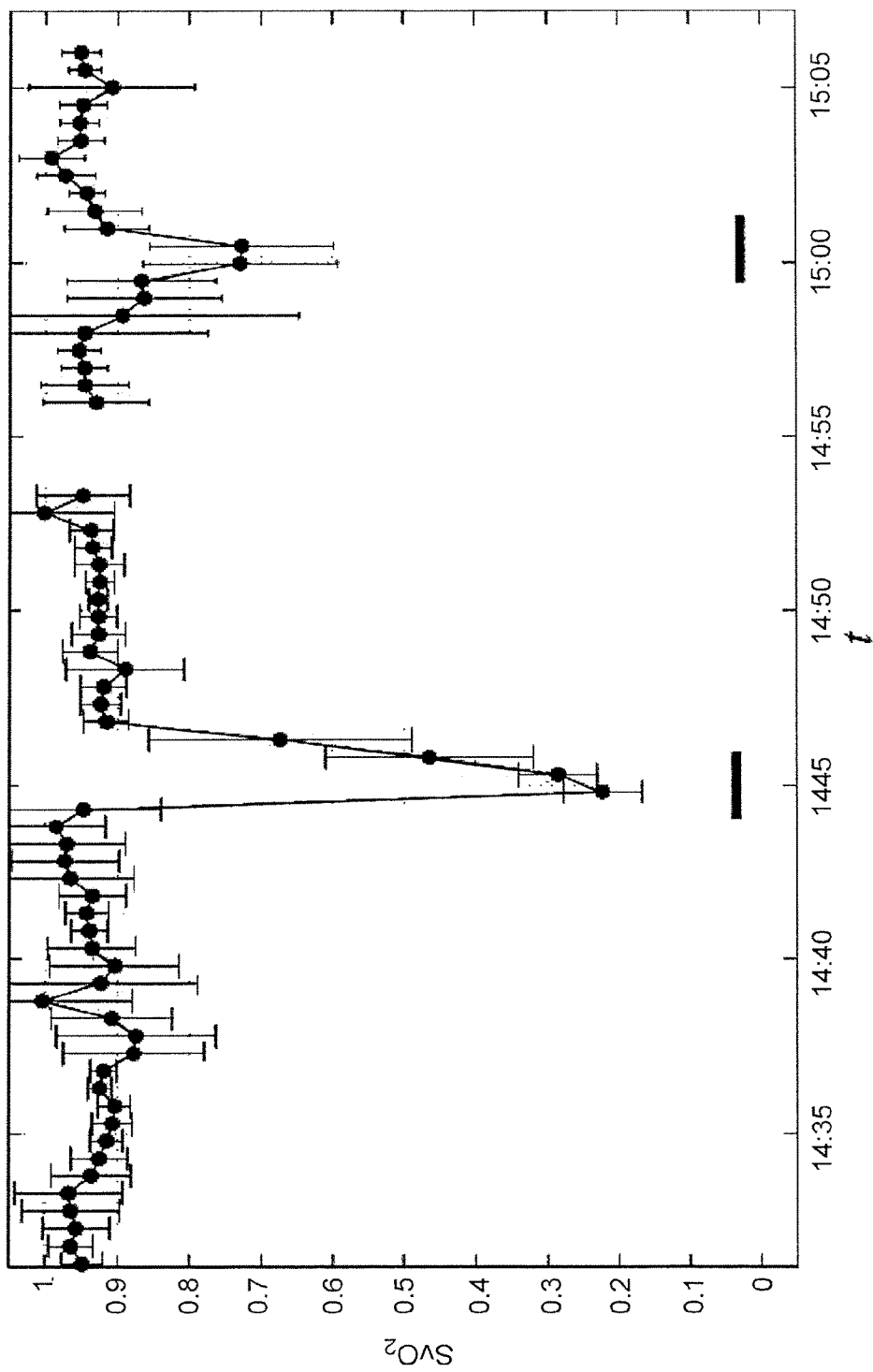
FIG. 7 shows a measurement of oxygenation changes during exercise.

FIG. 7 illustrates the oxygenation changes during intense exercise measured with the system 40. The horizontal axis t of FIG. 7 designates the time and the vertical axis $SvO_2$ designates the measured oxygenation of venous blood. The chosen example illustrates the oxygenation of venous blood dropping during an onset of an exercise. Two clearly visible negative peaks represent two drops at the onset of two sets of squats performed by a subject (a human volunteer) around the time 14:45 and the time 15:00 (marked with horizontal solid lines). FIG. 7 clearly shows that the system 40 is capable to measure the oxygenation of venous blood and that an oxygenation drop in the venous blood can clearly be related to movement of the subject, in this case to physical exercise in form of squats. The oxygenation of arterial blood would not feature such significant drops.

Figure 8:
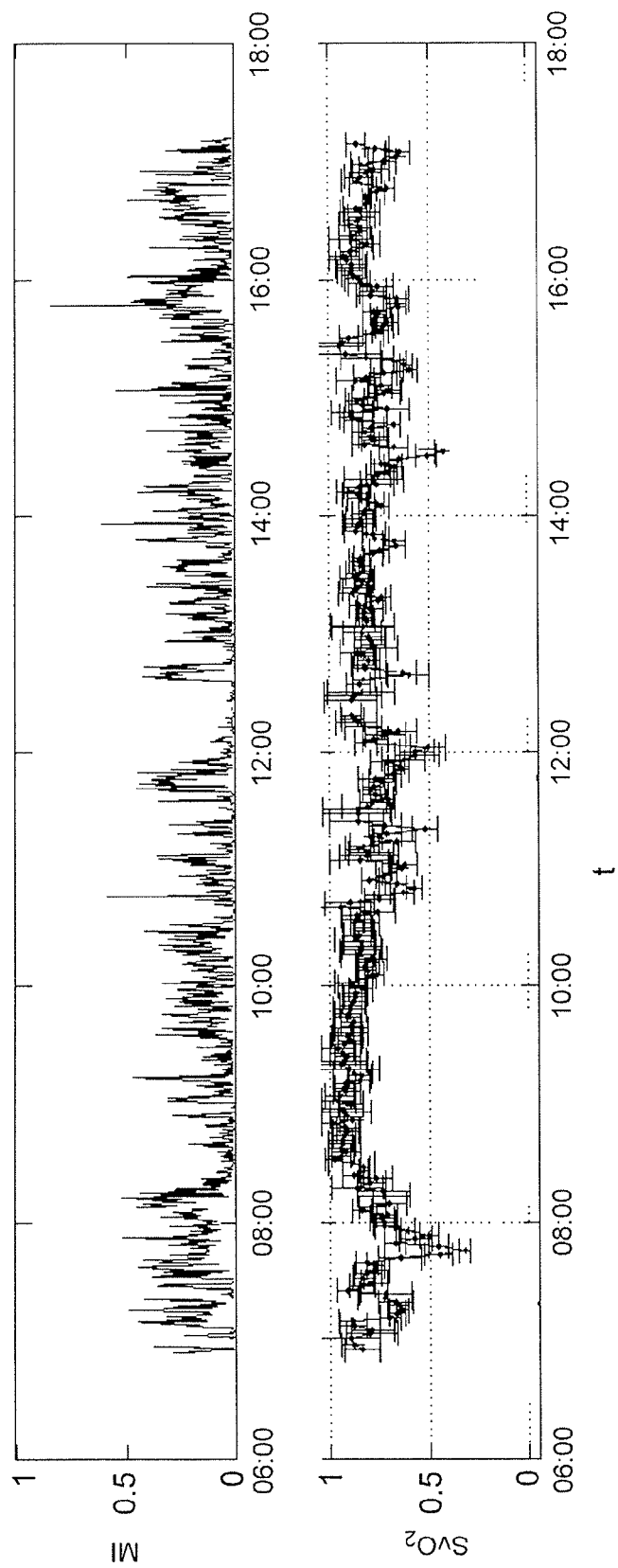
FIG. 8 shows a graph with an example of a venous oxygenation trace for one day and in another graph a corresponding trace of an acceleration sensor.

FIG. 8 shows an example continuous measurement with the system 40 of a subject, in this case a human volunteer performing normal life activities. An upper plot shows movements i.e. activities measured with accelerometer and a lower plot shows the corresponding venous oxygenation $SvO_2$. Both plots have a horizontal axis t designating time, and the vertical axis of the upper plot MI designates a calculated motion intensity parameter calculated from relative changes of a 3-axes accelerometer measurements while the vertical axis $SvO_2$ of the lower plot designates the oxygenation of venous blood. Drops in the oxygenation of the venous blood in a first time periods 7:35-8:14 and in a second time period 12:00-12:40 be related to physical activities (a bicycle ride to the office in the first time period and walking for lunch and back in the second time period).

Figure 9:
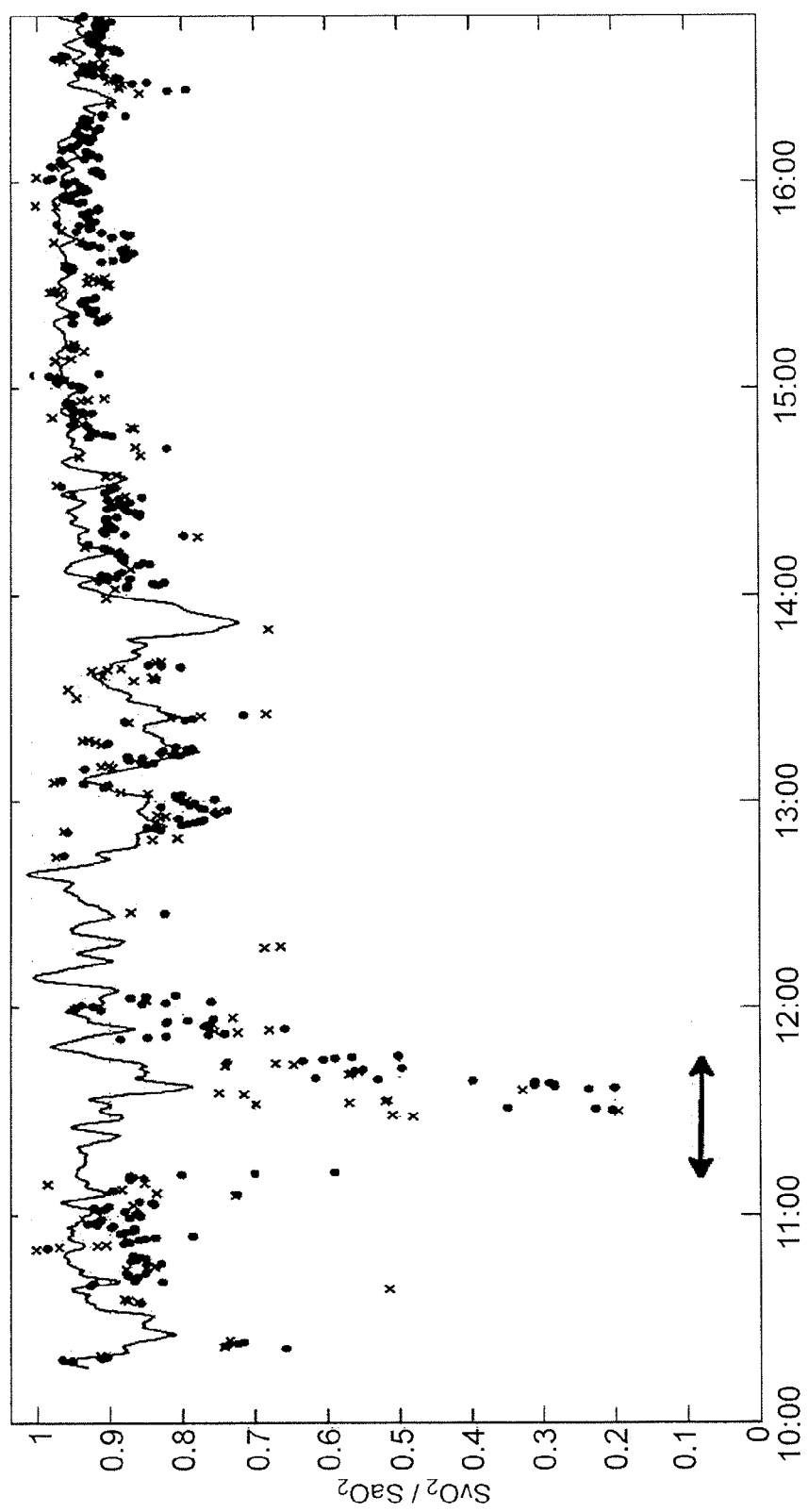
FIG. 9 shows in an upper graph the venous and arterial oxygenation over a day.

FIG. 9 shows the venous and arterial oxygenation of a person during a day. The horizontal axis t designates time and the vertical axis designates the arterial oxygenation $SaO_2$ as well as the venous oxygenation $SvO_2$:$SaO_2$ is shown with a solid line and $SvO_2$ is shown with symbols. Filled circles show the results of the $SvO_2$ estimation with a coefficient of determination $R^2$ of above 0.9, while crosses feature $R^2$ between 0.8 and 0.9. A negative peak of the venous oxygenation around time 11:30 (marked in FIG. 9 with a double headed horizontal arrow) was induced on purpose by an occlusion of the blood vessels in the tissue (the occlusion reduced the maximal blood pressure to 20-40 mmHg and was induced between 11:00 h and 11:40 h). The induced occlusion demonstrates clearly that the expected drop in oxygenation of the venous blood can be measured by the system 40. The oxygenation of the arterial blood does not indicate any significant events, while the drop in the oxygenation of the venous blood allows identifying the temporary induced occlusion.

Figure 10:
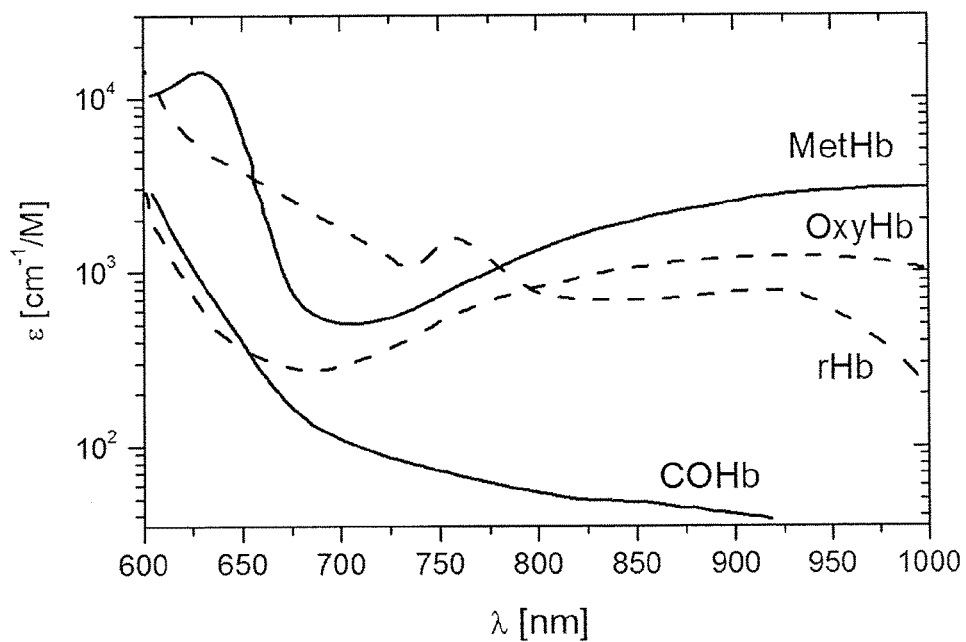
FIG. 10 shows a graph with the absorbance of different derivatives of hemoglobin in dependence of the wavelength of light.

FIG. 10 schematically shows a graph with the absorbance of different derivatives of hemoglobin in dependence of the wavelength of light. The vertical axis $\in$ of the graph represents the absorbance i.e. a molar extinction coefficient [$cm^{-1}$/M] which measures how strongly the hemoglobin derivative absorbs light. The horizontal axis $\lambda$ of the graph represents the wavelength [nm] of the light. The derivatives shown in FIG. 10 are methemoglobin (MetHb) and carboxyhemoglobin (COHb) represented by solid lines and oxyhemoglobin (oxyHb) and reduced hemoglobin (rHb) represented by broken lines. All derivatives vary strongly in the shown range of wavelength and can therefore be detected optically and discerned in measurements at wavelengths chosen appropriately.

While the invention has been described in present embodiments, it is distinctly understood that the invention is not limited thereto, but may be otherwise variously embodied and practised within the scope of the claims.

LIST OF DESIGNATIONS $\in$ molar extinction coefficient [$cm^{-1}$/M]
$\lambda$ wavelength [nm]
oxyHb oxygenated hemoglobin
rHb reduced hemoglobin
t time
I intensity Acc Y acceleration
r distance between light emitter and optical detector
S light emitter
D optical detector
Δ A (798) attenuation of infrared light
Δ A (660) attenuation of red light
MI calculated motion intensity parameter
$SvO_2$ oxygenation of venous blood
$SaO_2$ oxygenation of arterial blood
MetHb methemoglobin
COHb carboxyhemoglobin
oxyHb oxyhemoglobin
1 device
30.1, 30.2 initial arterial attenuation signal
31.1, 31.2 initial venous attenuation signal
32.1, 32.2 measured optical signals
33 accelerometer signal
34.1, 34.2 arterial portion signal
35.1, 35.2 venous portion signal
40 system
41 frame
42.1, 42.3 light detector compartment
42.2 light emitter compartment
43 glass plate
44 acceleration sensor
45 substrate
46.1-46.3 LEDs
47.1, 47.2 monitoring photo diode
48.1, 48.2 signal photo diode
49 photon path
50.1, 50.2 reflective element
51 tissue
60 human skin
61.1-61.4 skin layer
62 photon path

The invention claimed is:

1. A method for measurement of physiological properties of tissue comprising the steps of
    a) emitting light with at least two wavelengths,
    b) measuring an optical signal based on a light intensity after the emitted light has interacted with the tissue,
    c) performing an accelerometer measurement synchronized with the step of measuring an optical signal,
    d) evaluating a physiological property of venous blood from a combination of said optical signal and said accelerometer measurement,
wherein said step of evaluating the physiological property of venous blood comprises the step of statistically correlating said accelerometer measurement with said optical signal, and wherein said method further comprises the steps of determining portions of the optical signal correlated with the accelerometer measurement to be of venous origin and uncorrelated signal portions to be of arterial origin.

* * * * *